(12) United States Patent  (10) Patent No.: US 7,174,923 B2
Schorn et al.  (45) Date of Patent: Feb. 13, 2007

(54) REFILL KIT FOR AN IMPLANTABLE PUMP

(75) Inventors: Gregory Schorn, Milford, MA (US); Sevak Stephanian, Cranston, RI (US)

(73) Assignee: Codman & Shurtleff, Inc., Raynham, MA (US)

( * ) Notice: Subject to any disclaimer, the term of this patent is extended or adjusted under 35 U.S.C. 154(b) by 459 days.

(21) Appl. No.: 10/699,370

(22) Filed: Oct. 31, 2003

(65) Prior Publication Data

US 2005/0092387 A1    May 5, 2005

(51) Int. Cl.
  *B65B 1/04*  (2006.01)
(52) U.S. Cl. .............................. 141/2; 141/18; 141/27; 141/301; 604/416
(58) Field of Classification Search ................ 141/301, 141/302, 2, 18, 21–27; 604/111, 416
  See application file for complete search history.

(56) References Cited

U.S. PATENT DOCUMENTS 5,183,472 A    2/1993  Jaehrling
5,544,519 A *  8/1996  Hammarberg et al. ......... 73/37
6,360,784 B1   3/2002  Philippens

FOREIGN PATENT DOCUMENTS

GB         1297794 A    11/1972
WO    WO 01/36026 A     5/2001

OTHER PUBLICATIONS

Partial European Search Report EP04256699 dated Feb. 18, 2005.

* cited by examiner

*Primary Examiner*—Steven O. Douglas

(57) ABSTRACT

A kit for refilling an implantable pump includes a first syringe, a second syringe a a three-way stopcock, which has three ports and an actuator. The actuator allows for selectively effecting fluid communication between only two of the ports. The first syringe is in fluid communication with a first one of the ports. The second syringe is in fluid communication with a second one of the ports. A filling needle is in fluid communication with a third one of the ports. The actuator is selectively moveable between a first position where the first syringe is in fluid communication with the second syringe and the filling needle is isolated from fluid communication with the first syringe and the second syringe, and a second position where the second syringe is in fluid communication with the filling needle and the first syringe is isolated from fluid communication with the second syringe and the filling needle.

13 Claims, 3 Drawing Sheets

REFILL KIT FOR AN IMPLANTABLE PUMP

BACKGROUND OF THE INVENTION

1. Field of the Invention

The present invention relates to refill kits. More specifically, the present invention relates to a refill kit for an implantable pump having a fluid reservoir under high pressure.

2. Discussion of the Related Art

The implantable drug infusion pump (IDIP) has provided physicians with a powerful tool for administering a wide variety of drugs and other agents, such as pain killers, nerve growth factor, and anti-spasticity drugs, to very particularized sites within a patient's body, such as the intrathecal region of the spinal column. The IDIP has also freed some patients from the restrictions of typical intravenous drug infusion systems that typically include a wheeled cart that must be pulled around behind the patient.

An IDIP is ordinarily surgically implanted subcutaneously in the patient's abdomen. The IDIP has an internal reservoir for storing the drug or agent. After implantation, the drug or agent is delivered to a selected site in the patient's body via a catheter that is attached to the pump and tunneled subcutaneously to the selected site.

Before the IDIP can be implanted in the patient's body, it must be filled with the applicable drug or agent. For many long-term applications, the IDIP may have to be refilled while the pump is still implanted within the patient's body. This is normally done by passing the drug or agent through a hypodermic needle that has been pierced through the patient's skin and coupled to the subcutaneously disposed IDIP. However, before refilling the IDIP, any remaining drug or agent contained within the reservoir must first be emptied. Typically, the IDIP is emptied by simply connecting the filling needle to a collection syringe. Thereafter, the collection syringe is disconnected from the tube connected to the filling needle. The IDIP is then refilled in a conventional manner.

In an IDIP, a propellant gas is placed in a pressure chamber to apply a pressure to a reservoir that receives the drug or agent. The reservoir is typically defined by a bellows structure so that the volume of the reservoir may vary. The propellant gas acts as a pressure-providing means to the bellows structure that biases the bellows structure to discharge the drug or other agent stored in the reservoir. The propellant gas used to drive such a "gas driven" IDIP is a fluid that is in phase change between a liquid state and a gas state when, i.e., in equilibrium between phases at around 37 degrees (Celsius), which is the usual temperature of the human body. In IDIPs, the propellant gas is chosen to provide a pressure on the bellows structure of about 9 p.s.i. to about 36 p.s.i.

As mentioned above, when refilling the IDIP, the drug or other agent is passed from a syringe into the IDIP, where it enters into the reservoir. However, the drug or other agent must enter the reservoir at a pressure sufficient to overcome the pressure bias on the reservoir from the propellant gas in the pressure chamber. In some cases, the drug or other agent must be delivered to the reservoir at a pressure higher than 36 p.s.i.

Due to the principles of hydraulics, this 36 p.s.i. pressure is applied over the entire cross-sectional area of the plunger within the syringe. When refilling an IDIP, typically the entire reservoir capacity of the IDIP is refilled. A typical IDIP may have a reservoir volume of 20 ml, 40 ml or 50 ml. To refill an IDIP with, for example, a 50 ml reservoir, a pharmacy typically prepares 50 ml of the drug or other agent and places it in a pharmacy syringe corresponding in size to the amount of drug or other agent to be refilled, in this case, a 50 ml syringe. The 50 ml pharmacy syringe could be coupled directly to the IDIP.

As is well known, the cross-sectional area of the plunger of a relatively small syringe such as a 10 ml syringe is smaller than the cross-sectional area of a larger syringe such as a 50 ml syringe. As a result, the force needed to apply 36 p.s.i. to drug or other agent in a syringe is determined by multiplying 36 p.s.i. by the cross-sectional area of the plunger. In the case of a 50 ml syringe, this total force is on the order of 25 pounds. This is a larger force than many people are able to generate with their hands. On the other hand, because the cross-sectional area of a 10 ml syringe is substantially smaller than the cross-sectional area of a 50 ml syringe, the total force needed to apply apply 36 p.s.i. to drug or other agent in a 10 ml syringe is about 6 pounds. This force is well within the range of force that most people can generate with their hands.

As a result, many practitioners, when refilling large reservoir pumps such as the 50 ml reservoir pumps, require the pharmacy to place the 50 ml of the drug or other agent to be refilled into several smaller syringes such as 10 or 20 ml syringes instead of in one large syringe. These smaller syringes allow the practitioner to apply the drug or other agent to the reservoir even in pumps that have relatively high gas propellant pressures in their pressure chambers. Unfortunately, using several smaller syringes instead of one large syringe means that each syringe must be attached and disconnected from the inlet each time instead of once as would be the case for the larger syringe. With this increased number of connections and disconnections, there is an increased chance of infection entering the system or other problems occurring.

U.S. Pat. No. 6,360,784 to Philippens et al. discloses a valved connector that solves some of these problems by providing a system that allows the practitioner to provide the drug or other agent to the reservoir of the IDIP while minimizing the number of times the sterile connection between the pharmacy syringe and the system is broken. But Philippens requires the application of a manual clamp in the filling tube line which must be opened and closed at specific times during the refilling cycle to permit Philippens' system to operate properly. Also, Philippens' incorporates a one-way valve 60 in a connector that must be located in a central lumen between the first inlet port from the first syringe and a point where the second inlet port from the second syringe connects to the central lumen. The one-way valve is biased to allow fluid to pass only from the first inlet port to the central lumen, and never from the second inlet port to the first inlet port.

In view of the foregoing, it is desirable to provide a system that allows the practitioner to easily empty the reservoir and thereafter provide the drug or other agent to the reservoir of the IDIP. The present invention is directed to overcoming the aforementioned disadvantages.

SUMMARY OF THE INVENTION

These and other objects of the present invention are achieved with a kit for refilling an implantable pump that includes a first syringe, a second syringe a a three-way stopcock, which has three ports and an actuator. The actuator allows for selectively effecting fluid communication between only two of the ports. The first syringe is in fluid communication with a first one of the ports. The second syringe is in fluid communication with a second one of the ports. A filling needle is in fluid communication with a third one of the ports. The actuator is selectively moveable between a first position where the first syringe is in fluid communication with the second syringe and the filling needle is isolated from fluid communication with the first syringe and the second syringe, and a second position where the second syringe is in fluid communication with the filling needle and the first syringe is isolated from fluid communication with the second syringe and the filling needle.

BRIEF DESCRIPTION OF THE DRAWING FIGURES

The above and still further objects, features and advantages of the present invention will become apparent upon consideration of the following detailed description of a specific embodiment thereof, especially when taken in conjunction with the accompanying drawings wherein like reference numerals in the various figures are utilized to designate like components, and wherein.

DETAILED DESCRIPTION OF THE PRESENTLY PREFERRED EXEMPLARY EMBODIMENTS

Figure 1:
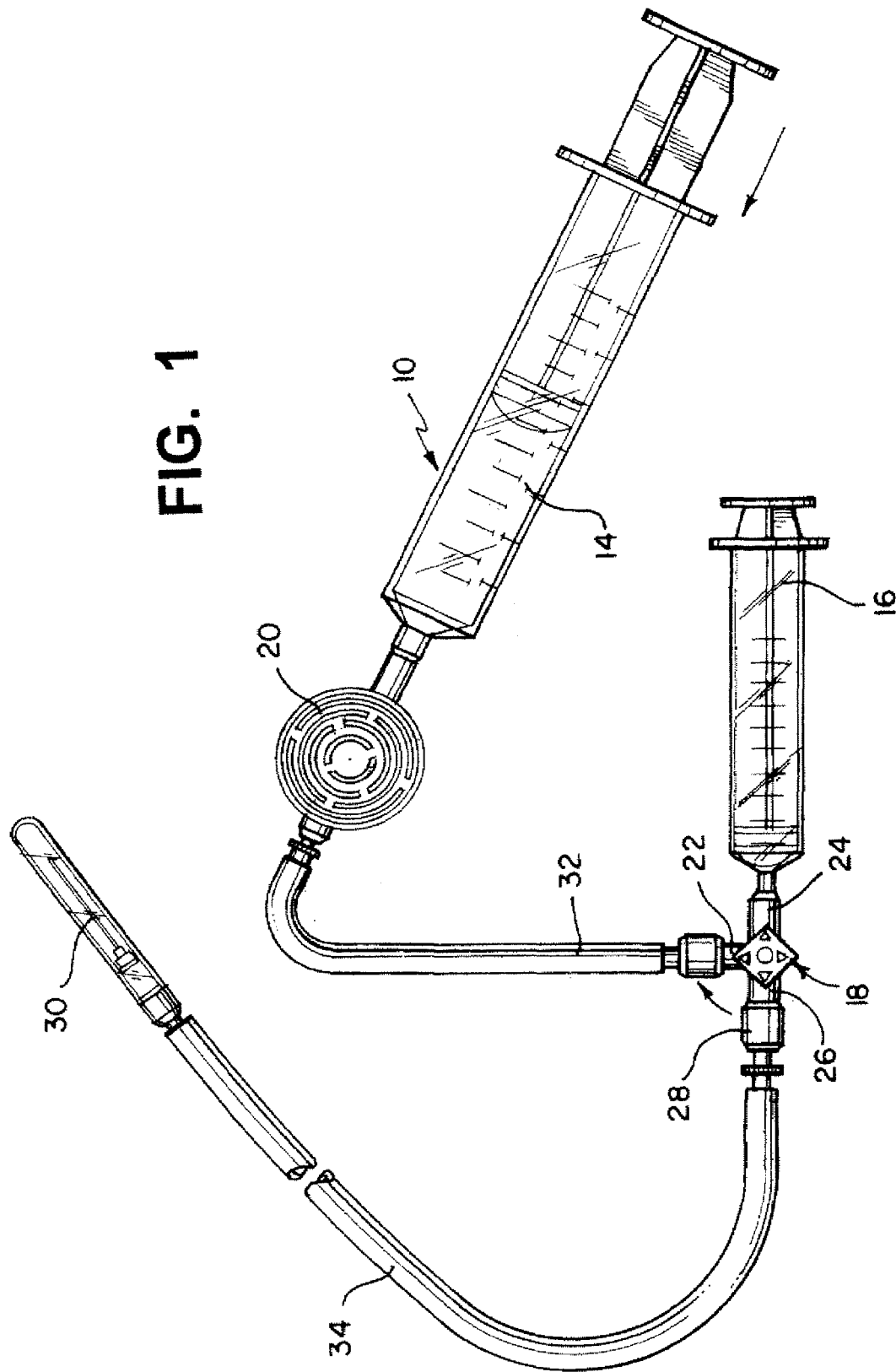
FIG. 1 is a plan view of a kit for refilling an implantable pump in accordance with the present invention showing the second syringe being filled with a drug or agent.
Figure 2:
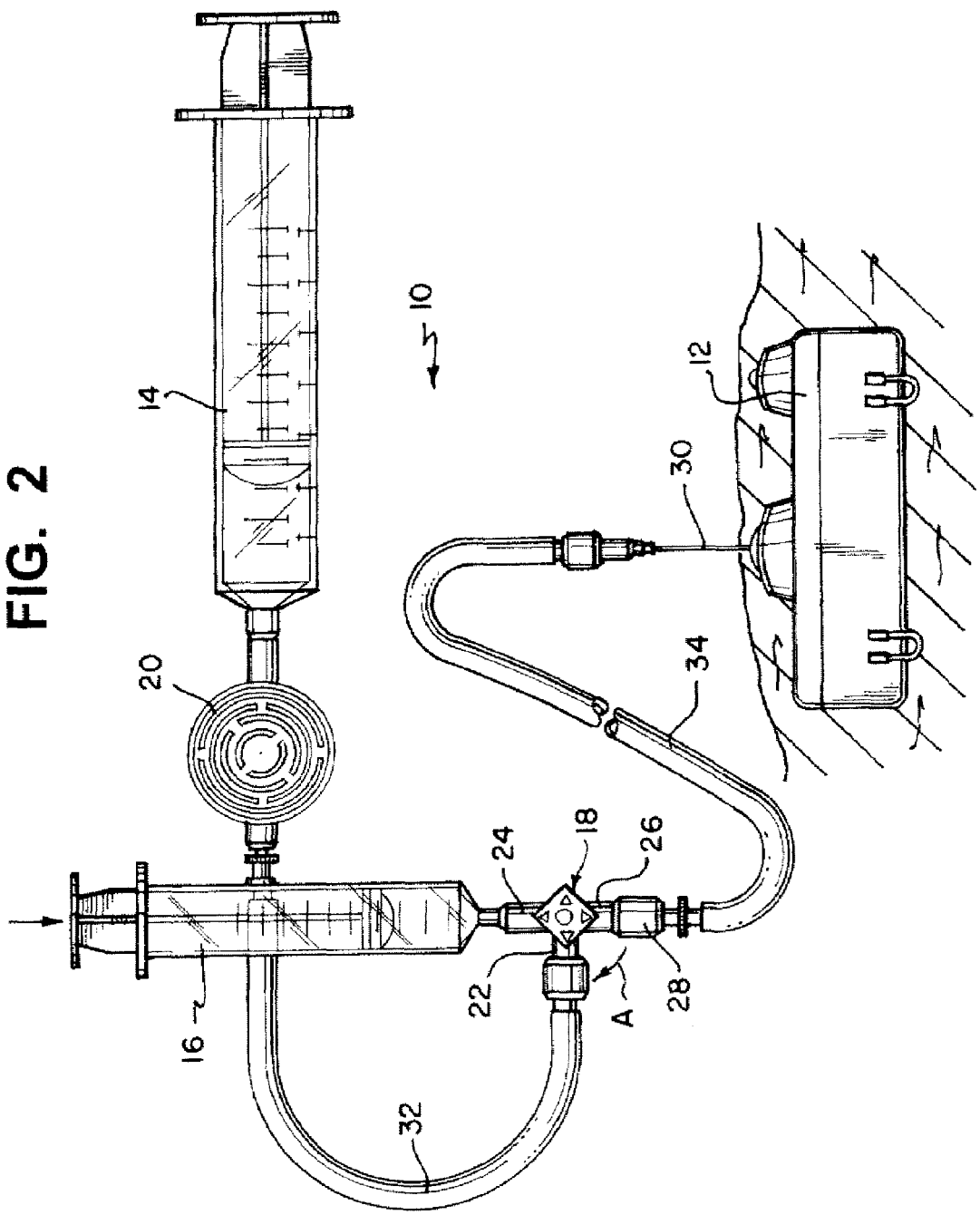
FIG. 2 is a plan view of a kit for refilling an implantable pump showing the second syringe in the process of filling an implanted pump with a drug or agent.
Figure 3:
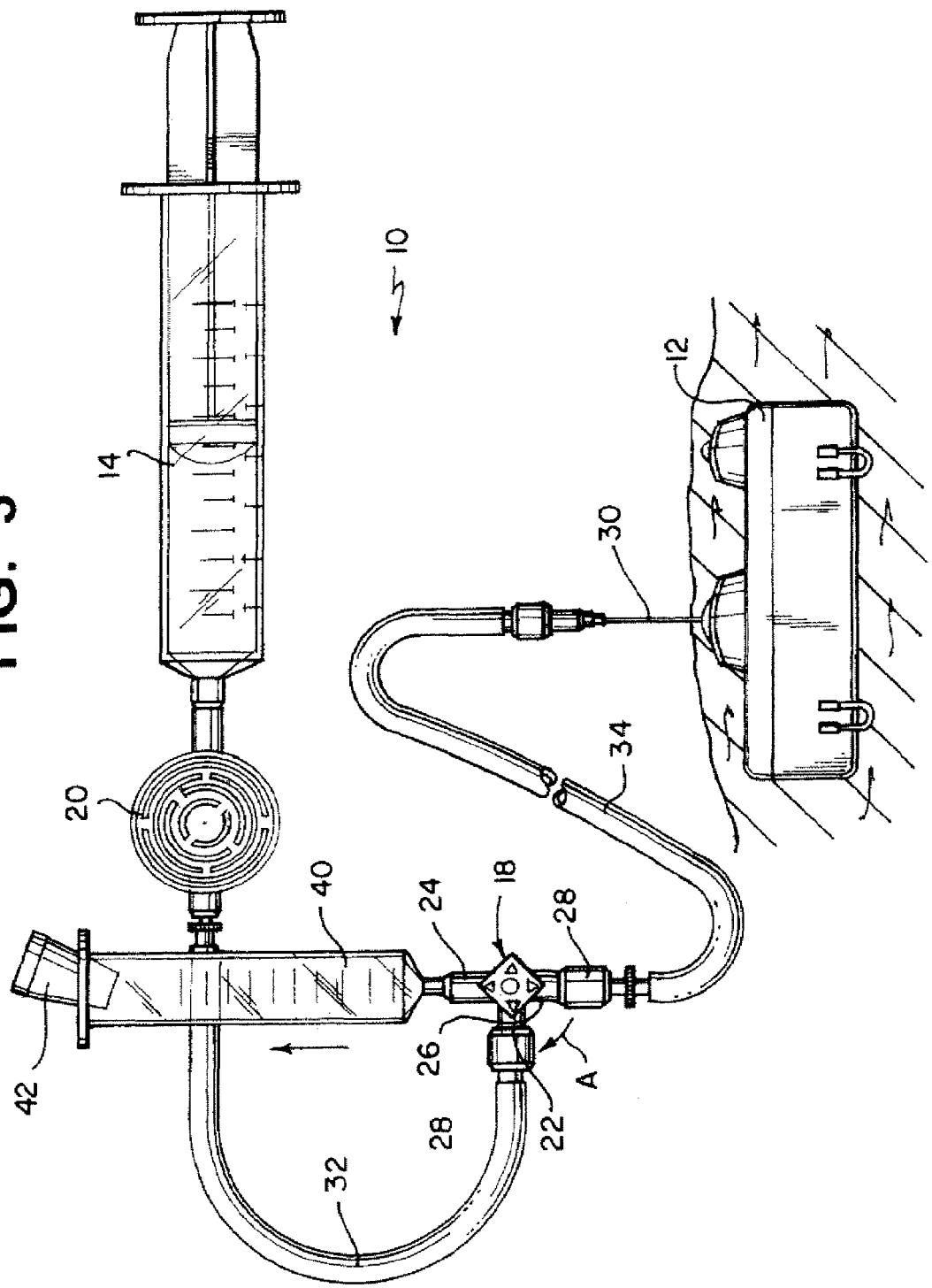
FIG. 3 is a plan view of a kit for refilling an implantable pump showing the pump reservoir being emptied.

Referring now to FIGS. 1–3, a kit 10 for refilling an implantable pump 12 is illustrated. Kit 10 includes a first syringe 14, a second syringe 16, a three-way stopcock 18 and a filter 20. The three-way stopcock has three ports 22, 24, 26 and an actuator 28 for selectively effecting fluid communication between only two of the ports. The first syringe 14 is in fluid communication with the first port 22. The second syringe 16 is in fluid communication with the second port 24.

A filling needle 30 is in fluid communication with the third port 26. Actuator 28 is selectively moveable between a first position, as shown in FIG. 1, where the first syringe 14 is in fluid communication with the second syringe 16 and the filling needle 30 is isolated from fluid communication with the first syringe 14 and the second syringe 16, and a second position, as illustrated in FIG. 2 after the actuator 28 is moved 90° in the direction indicated by arrow A, where the second syringe 16 is in fluid communication with the filling needle 30 and the first syringe 14 is isolated from fluid communication with the second syringe 16 and the filling needle 30.

The first syringe 14 is preferably a 50 to 60 ml syringe and the second syringe is preferably a 10 ml syringe.

As illustrated in the drawing figures, the first syringe 14 is preferably in fluid communication with the first port 22 by way of a connecting tube 32. The second syringe 16 is preferably directly in fluid communication with the second port 24. The filling needle 30 is preferably placed in fluid communication with the third port 26 by way of a connecting tube 34. All of the connections are preferably made by a luer lock connection, which is well known to those skilled in the art.

If the pump 12 is implanted and in use, then its reservoir should be emptied before being refilled so that the practitioner will know much medication has been delivered. Additionally, should a different concentration or a different drug needs to be delivered it will be necessary to empty the reservoir first, and preferably to thereafter rinse the reservoir as well. Referring now to FIG. 3, to empty the reservoir a collection syringe 40 is connected to the second port 24, and a silicone stopper 42 is firmly placed onto the open end of syringe 40. The stopcock actuator 28 is placed in the first position. The filling needle 30 can then be inserted into the pump's reservoir in a conventional manner. The stopper 42 can then be loosened, and the stopcock actuator 28 is then moved in the direction indicated by arrow A to the second position. The contents of the reservoir will then collect in the collection syringe due to the force applied on the reservoir by the gas propellant within pump 12. Once the reservoir is empty, actuator 28 is moved back to the first position. The practitioner can then remove the collection syringe 40 from the second port 24 and record the volume of fluid removed from the reservoir.

In some instances, the practitioner may determine that it is preferable to rinse the reservoir with saline prior to refilling the reservoir. In such a case the three-way stopcock of the present invention permits this operation to be completed rather easily, just as the stopcock permitted the emptying of the reservoir to be completed in a simple manner, all while using the same structure that is used to refill the reservoir. To rinse the reservoir, the user can preferably obtain two 10-mL syringes, each containing 5 mL of saline (not shown). The first of the saline filled syringes is connected to the second port 24 of the stopcock 18. The stopcock handle 28 is placed in the second position. The saline is slowly injected into the reservoir. Thereafter, the user can remove pressure from the syringe plunger and allow the saline to reflux into the syringe. The stopcock handle 28 is then turned to the first position. The first syringe can then be removed from the second port 24 and discarded with the refluxed solution appropriately. The second saline filled syringe is then connected to the second port 24 of the stopcock 18. The stopcock handle 28 is then moved to the second position. The saline from the second syringe is then slowly injected by the user into the reservoir. Thereafter, the user can remove pressure from the second syringe plunger and allow the saline to reflux into the second syringe. The stopcock handle 28 is then turned to the first position. The second syringe can then be removed from the second port 24 and discarded with the refluxed solution appropriately.

To initially fill or to refill the reservoir of the implanted pump 12 (hereinafter collectively referred to as refilling), the user will connect the first syringe 14 to the first one of the ports 22. The second syringe 16 is then connected to the second one of the ports 24. The filling needle 30, if not done so already, is connected to the third one of the ports 26. The filling needle 30 is placed in an implantable pump 12 in fluid communication with the reservoir of the implantable pump. The three way stopcock 18 is placed in a first position where the first syringe 14 is in fluid communication with the second syringe 16 and the filling needle 30 is isolated from fluid communication with the first syringe 14 and the second syringe 16, as shown in FIG. 1. Fluid is drawn from the first syringe 14 into the second syringe 16 by depressing the first syringe's plunger, by withdrawing the second syringe's plunger, or a combination of both actions. After drawing the fluid from the first syringe 14 into the second syringe 16, the handle 28 of the three way stopcock is moved to a second position, as indicated by arrow A in FIG. 2, where the second syringe 16 is in fluid communication with the filling needle 30 and the first syringe 14 is isolated from fluid communication with the second syringe 16 and the filling needle 14, as illustrated in FIG. 2. The plunger of the second syringe 16 is depressed thereby causing fluid to be expelled from the second syringe 16 through the filling needle 30 into the implantable pump reservoir. Because the plunger of the second syringe 16 has a smaller cross-sectional area than the plunger of first syringe 14, the operator is able to manually apply the required force to depress the second syringe's plunger to overcome the pressure placed upon the reservoir within the IDIP, thereby filling the reservoir with a drug or other agent.

Thereafter, the stopcock 18 is moved back to the first position and the cycle will be repeated as often as necessary to refill the reservoir of the implantable pump.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps which perform substantially the same function, in substantially the same way, to achieve the same results are within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

What is claimed is:

1. A kit for refilling an implantable pump comprising:
   a first syringe;
   a second syringe;
   a collection syringe;
   a three-way stopcock having three ports and an actuator for selectively effecting fluid communication between only two of said ports, said first syringe being selectively in fluid communication with a first one of said ports, said second syringe being selectively in fluid communication with a second one of said ports, said collection syringe being selectively in fluid communication with said second one of said ports;
   a filling needle being in fluid communication with a third one of said ports;
   wherein said actuator is selectively moveable between a first position where the first syringe is in fluid communication with said second syringe and the filling needle is isolated from fluid communication with the first syringe and the second syringe, and a second position where the second syringe is in fluid communication with the filling needle and the first syringe is isolated from fluid communication with the second syringe and the filling needle.

2. The kit according claim 1, further comprising a filter being in fluid communication with said first syringe and said first one of said ports.

3. The kit according claim 1, wherein the first syringe is a 50 ml syringe and said second syringe is a 10 ml syringe.

4. The kit according claim 1, further comprising a stopper being placed on an open end of said collecting syringe.

5. A system comprising:
   an implantable pump having a reservoir and a refill port; and
   a kit for refilling an implantable pump comprising:
   a first syringe;
   a second syringe;
   a collection syringe;
   a three-way stopcock having three ports and an actuator for selectively effecting fluid communication between only two of said ports, said first syringe being in fluid communication with a first one of said ports, said second syringe being in fluid communication with a second one of said ports, said collection syringe being selectively in fluid communication with said second one of said ports;
   a filling needle being in fluid communication with a third one of said ports, said filling needle having a distal end adapted for fluid communication with the reservoir of the implantable pump for filling the reservoir;
   wherein said actuator is selectively moveable between a first position where the first syringe is in fluid communication with said second syringe and the filling needle is isolated from fluid communication with the first syringe and the second syringe, and a second position where the second syringe is in fluid communication with the filling needle and the first syringe is isolated from fluid communication with the second syringe and the filling needle.

6. The system according to claim 5, further comprising a filter being in fluid communication with said first syringe and said first one of said ports.

7. The system according claim 5, wherein the first syringe is a 50 ml syringe and said second syringe is a 10 ml syringe.

8. The kit according claim 5, further comprising a stopper being placed on an open end of said collecting syringe.

9. A method of refilling a reservoir of an implantable pump by transferring fluid from a first syringe to a second syringe and from the second syringe to a reservoir of an implantable pump, comprising the steps of:
   providing an implantable pump refilling system comprising:
   a first syringe;
   a second syringe;
   a three-way stopcock having three ports and an actuator for selectively effecting fluid communication between only two of said ports, said first syringe being selectively in fluid communication with a first one of said ports, said second syringe being selectively in fluid communication with a second one of said ports; and
   a filling needle being in fluid communication with a third one of said ports;
   connecting the first syringe to the first one of the ports;
   connecting the second syringe to the second one of the ports;
   connecting the filling needle to the third one of the ports;
   placing the filling needle in an implantable pump in fluid communication with the reservoir of the implantable pump;
   placing the three way stopcock in a first position where the first syringe is in fluid communication with said second syringe and the filling needle is isolated from fluid communication with the first syringe and the second syringe;
   drawing fluid from the first syringe into the second syringe;
   after the drawing fluid from the first syringe into the second syringe step, placing the three way stopcock in a second position where the second syringe is in fluid communication with the filling needle and the first syringe is isolated from fluid communication with the second syringe and the filling needle;

depressing the plunger of the second syringe whereby fluid is expelled from the second syringe through the filling needle into the implantable pump reservoir; and repeating the steps of placing the three way stopcock in a first position, drawing fluid from the first syringe into the second syringe, after the drawing fluid from the first syringe into the second syringe step, placing the three way stopcock in a second position, and depressing the plunger of the second syringe as many times as necessary to refill the pump reservoir.

10. The method according to claim 9, further comprising the steps of:

before the connecting the second syringe step, placing the three-way stopcock in the first position;

connecting a collection syringe to the second one of the ports;

placing the three-way stopcock in the second position;

collecting the contents of the reservoir in the collecting syringe.

11. The method according to claim 10, further comprising the steps of:

after the collecting step, placing the three-way stopcock in the first position;

removing the collecting syringe from the second one of said ports.

12. The method according to claim 11, further comprising the steps of:

after the removing the collecting syringe step, connecting a saline filled syringe to the second one of said ports;

placing the three-way stopcock in the second position;

injecting the saline from the saline filled syringe into the reservoir;

permitting the saline to reflux back into the saline filled syringe;

placing the three-way stop-cock in the first position;

removing the saline filled syringe from the second one of said ports.

13. The method according to claim 12, further comprising the steps of:

after the removing the saline filled syringe step, connecting a second saline filled syringe to the second one of said ports;

placing the three-way stopcock in the second position;

injecting the saline from the second saline filled syringe into the reservoir;

permitting the saline to reflux back into the second saline filled syringe;

placing the three-way stop-cock in the first position;

removing the second saline filled syringe from the second one of said ports.

* * * * *